United States Patent [19]

Rynbrandt et al.

[11] Plant 5,096

[45] Aug. 30, 1983

[54] BLACK SWEET CHERRY

[75] Inventors: Cecil Rynbrandt; John Rynbrandt, both of Dorr, Mich.

[73] Assignee: Hilltop Orchards & Nurseries, Inc., Hartford, Mich.

[21] Appl. No.: 309,586

[22] Filed: Oct. 8, 1981

[51] Int. Cl.[3] ..... A01H 5/00

[52] U.S. Cl. ..... Plt./37

[58] Field of Search ..... Plt./37

*Primary Examiner*—Robert E. Bagwill

*Attorney, Agent, or Firm*—John R. Nesbitt

[57] ABSTRACT

This invention relates to a new and distinct variety of black sweet cherry which occurred as a chance seedling in a cultivated area, which was a cherry orchard having predominately Schmidt black sweet cherry trees growing around it. The new variety most nearly resembles Schmidt in size and appearance. It is distinctively characterized, in comparison to Schmidt, by at least seven days earlier maturity, a shorter harvest period and leaves that are shorter and narrower.

1 Drawing Figure

GENERAL DESCRIPTION OF THE NEW VARIETY

This invention is a new and distinct cultivar of cherry tree, discovered as a seedling in a cultivated area on the farm of Cecil and John Rynbrandt, on the North half (N ½) of Section 8, in Salem Township, Allegan County, Mich.

The new variety was asexually reproduced by Hilltop Orchards & Nurseries, Inc., and was given the experimental designation CR-403. Reproduction was both by budding and grafting from the parent tree and the trees produced are growing at the Hilltop farm at RFD#2, Hartford, Mich.

The tree bears a general resemblance to the Schmidt cherry in size and appearance (although the fruit itself is not as pointed as Schmidt) but the tree has shorter, narrower leaves and has a slightly earlier harvest period. The fruit is of excellent quality and has a firm texture.

DETAILED DESCRIPTION OF THE NEW VARIETY

Tree

Figure 1:
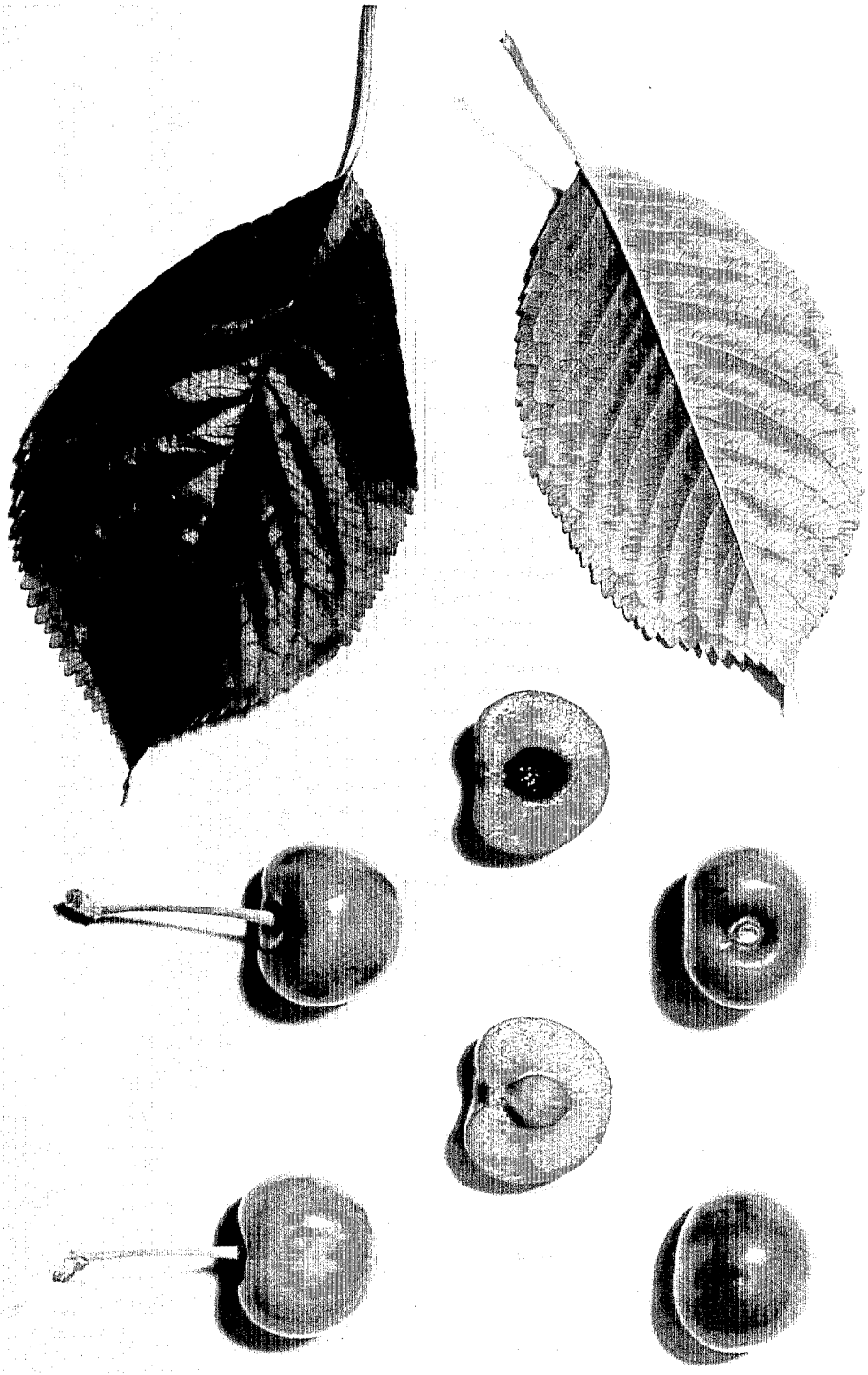
FIG. 1 is a color photograph having a side view of a cherry with stem intact, a section elevation with the stone remaining in place, a top view of a cherry with stem removed and top and bottom views of the leaf.

General: Upright spreading, sturdy and heavily branched, similar to Schmidt but more vigorous and slightly taller at maturity. It appears more leafy than Schmidt and the new growth tips are fairly light but with some color present.

Bark: Greenish tan with prominent lenticels.

Leaf

Color: Dark green, more glossy than Schmidt (7.56Y 6/8 strong yellow green Munsell hue color chart).

Shape: Shorter and more rounded than Schmidt.

Size: Ratio of length to width is 2:1.

Petiole: Short, thick and attachment more upright than Schmidt, margin serations are more rounded and smooth than Schmidt.

Glands: Round to slightly oval.

Flower

General: White, medium size and showy, the petals separate with no tendency toward doubling. Bloom period is early to mid season. The period of bloom is average.

Fruit

Form: Uniform; symmetrical; globose to slightly oblate.

Suture: Shallow and light colored.

Ventral surface: Rounded slightly.

Skin: Smooth and somewhat waxy, thickness is medium, texture is tough to medium, tendency to crack — none.

Pit: Small, roundish, flat, size 0.8 cm×1.0 cm, and is partially freestone.

Flesh: The texture is dark red and firm, crisp; meaty; with an excellent quality and a fruity aroma.

Maturity season: The fruit ripens evenly at least 7 days ahead of Schmidt variety.

Color: Distinctive mahogany colored (5R 2/6S dark red Munsell hue color chart) with lighter color at the sutures.

We claim:

1. A new and distinct variety of black sweet cherry tree substantially as described and illustrated in this application.

* * * * *